(12) United States Patent
Tanimoto et al.

(10) Patent No.: US 9,173,799 B2
(45) Date of Patent: Nov. 3, 2015

(54) URINE DISPOSAL DEVICE

(75) Inventors: Kei Tanimoto, Kagawa (JP); Hiroko Endo, Kagawa (JP); Miou Suzuki, Kagawa (JP)

(73) Assignee: Unicharm Corporation, Ehime (JP)

( * ) Notice: Subject to any disclaimer, the term of this patent is extended or adjusted under 35 U.S.C. 154(b) by 241 days.

(21) Appl. No.: 13/991,251

(22) PCT Filed: Dec. 19, 2011

(86) PCT No.: PCT/JP2011/079287
§ 371 (c)(1),
(2), (4) Date: Jun. 3, 2013

(87) PCT Pub. No.: WO2012/098796
PCT Pub. Date: Jul. 26, 2012

(65) Prior Publication Data
US 2014/0182051 A1    Jul. 3, 2014

(30) Foreign Application Priority Data
Jan. 21, 2011 (JP) ................................ 2011-011411

(51) Int. Cl.
A47K 11/00 (2006.01)
A61G 9/00 (2006.01)
A61F 5/44 (2006.01)
A61F 5/453 (2006.01)
A61F 5/451 (2006.01)

(52) U.S. Cl.
CPC . A61G 9/006 (2013.01); A61F 5/44 (2013.01); A61F 5/451 (2013.01); A61F 5/453 (2013.01)

(58) Field of Classification Search
CPC .......... A61G 9/006; A61F 5/44; A61F 5/451; A61F 5/453
USPC .................................................. 604/393, 402
See application file for complete search history.

(56) References Cited

U.S. PATENT DOCUMENTS

| 4,747,166 A * | 5/1988 | Kuntz ............................ 4/144.3 |
| 6,129,718 A | 10/2000 | Wada |
| 2004/0236292 A1 | 11/2004 | Tazoe et al. |
| 2007/0038194 A1 | 2/2007 | Wada et al. |

FOREIGN PATENT DOCUMENTS

| JP | 3065293 | 10/1999 |
| JP | 2000-201959 | 7/2000 |

(Continued)

OTHER PUBLICATIONS

International Search Report from corresponding PCT application No. PCT/JP2011/079287 dated Jan. 24, 2012 (4 pgs).

*Primary Examiner* — Tuan N Nguyen
(74) *Attorney, Agent, or Firm* — Brinks Gilson & Lione

(57) ABSTRACT

A urine disposal device for use with a urine detecting device that provides for smooth urination without compressing the wearer's urethra so that urination may be surely detected and voided urine may be quickly discharged out of the urine disposal devices. The urine disposal device has a front-back direction and includes a urination area having a first surface portion and a second surface portion cooperating to cover the penis of a wearer from the front-back direction and an opening through which the penis is inserted. The urination area has a urine collecting container provided in the second surface portion and the second surface portion lies on the side of the wearer's body.

14 Claims, 14 Drawing Sheets

(56) References Cited

FOREIGN PATENT DOCUMENTS

| | | |
|---|---|---|
| JP | 2002-509462 A | 3/2002 |
| JP | 2004-041697 | 2/2004 |
| JP | 3611429 | 10/2004 |
| JP | 2007-44494 A | 2/2007 |
| JP | 4316902 | 5/2009 |
| WO | WO 98/48753 | 11/1998 |

* cited by examiner

FIG.7
(a)
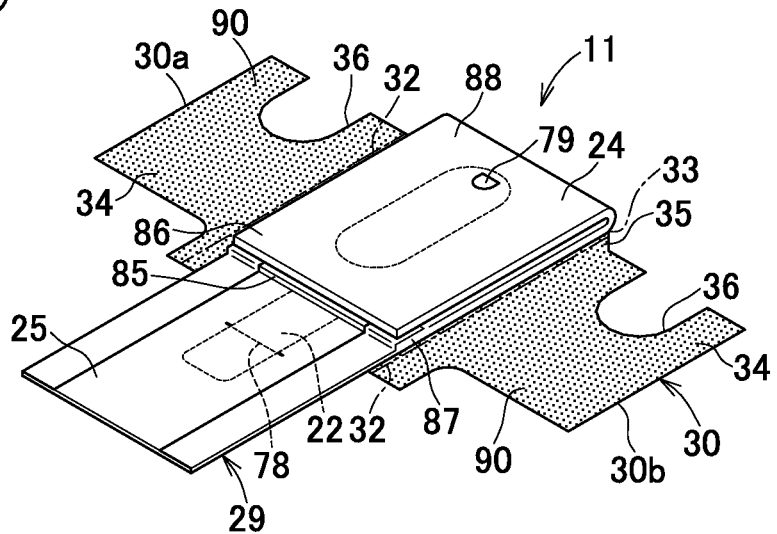
(b)
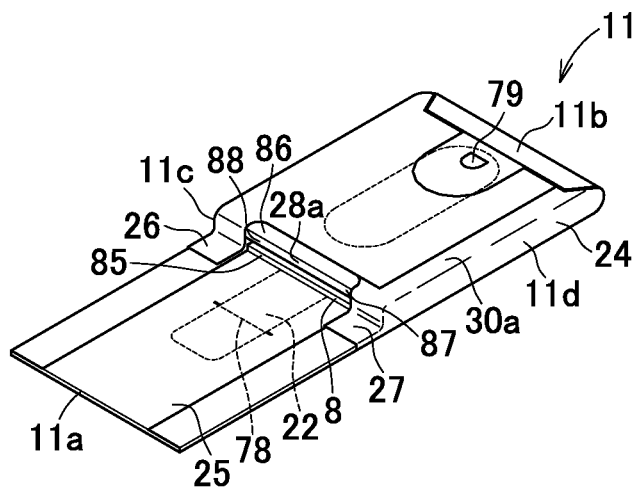

URINE DISPOSAL DEVICE

RELATED APPLICATION

This application is a 35 U.S.C. §371 national phase filing of International Patent Application No. PCT/JP2011/079287, filed Dec. 19, 2011, through which and to which priority is claimed under 35 U.S.C. §119 to Japanese Patent Application No. 2011-011411, filed Jan. 21, 2011.

TECHNICAL FIELD

The present invention relates to urine disposal devices for use with urine detecting devices allowing voided urine to automatically dispose of and more particularly to urine disposal devices for use with urine detecting devices including sensors to detect urine, for the purpose of quickly disposing of voided urine.

BACKGROUND

Conventionally, urine disposal devices used with the urine detecting devices adapted for automatically dealing with voided urine are known. For example, PTL 1 (JP 2004-41697 A) discloses a urine detecting device including a diaper provided with a urine sensor and a control unit adapted to receive a detection signal transmitted from the urine sensor. Aside from this, PTL 2 (JP 2000-201959 A) discloses a urine-absorbent pad provided with an opening for inserting and holding the wearer's penis.

CITATION LIST

Patent Literature

{PTL 1}: JP 2004-41697 A
{PTL 2}: JP 2000-201959 A

SUMMARY

Technical Problem

According to the urine detecting device disclosed in PTL 1, when urination occurs within the diaper, the detection signal transmitted from the urine sensor is received by an external device whereby a care person being away from the wearer may be informed of urination and may quickly perform necessary handling such as diaper exchange. In addition, on the basis of analysis result of the voided urine, the incontinent patient's physical condition may be checked and the incontinence curative drug's effect may be confirmed.

However, the urine sensor is located in the crotch region of the diaper and, in consequence, there is a likelihood that the urine sensor might response to body exudates other than urine, for example, loose passage and transmit the detection signal to an external device. For this reason, it is difficult for this urine sensor to limit the detection object to urine. In addition, if urine is voided on the electrodes of the urine sensor, an accurate function of the urine sensor might be disturbed.

In the urine-absorbent pad disclosed in PTL 2, the wearer's penis may be directly inserted into an opening formed in the pad main body to ensure that voided urine is exclusively absorbed and contained, and a region surrounding the opening is formed as a low stiffness region being free from any influence of external force exerted on the pad main body, whereby the wearer's penis is stabilized in its inserted state.

However, even with such urine-absorbent pad put on the wearer's body, a voided volume of urine and an excretion speed might exceed upper limits of absorbing performance and absorption speed of the absorbent core set in the pad main body and an excessive volume of urine might leak out from the opening. In addition to this problem, when such urine-absorbent pad is put on a wearer lying on the back, the own weight of urine voided on and absorbed by the pad main body might be loaded on the penis held by the opening's periphery to constrict the wearer's urethra and/or to press the scrotum against the urethra. In each case, an uncomfortable feeling against the wearer might be created and/or smooth urination might be disturbed.

An object of the present invention is to provide a urine disposal device used with a urine detecting device improved so that smooth urination may be ensured without compressing the urethra, urination may be surely detected and voided urine may be quickly discharged out of the urine disposal devices.

Solution to Problem

The present invention relates to a urine disposal device used with a urine detecting device including a urine sensor adapted to detect urination.

The present invention further including the following features:

the urine disposal device has a front-back direction and includes a urination area having a first surface portion and a second surface portion cooperating to cover the penis of a wearer in the front-back direction and an opening extending in a width direction of the urination area through which the penis is inserted, and the urination area has a urine collecting container and the second surface portion lies on the side of the wearer's body.

According to one embodiment of the present invention, an opening's periphery in at least one of the first and second surface portions is provided with an elastic rebound member extending in the urination area.

According to another embodiment of the present invention, the opening's periphery provided with the elastic rebound member is provided with a leakage-barrier having a predetermined thickness.

According to still another embodiment of the present invention, the urine disposal device has a longitudinal direction and the first surface portion extends outwardly in the longitudinal direction beyond the second surface portion.

According to yet another embodiment of the present invention, the leakage-barrier is a fibrous nonwoven fabric layer composed of a plurality of fibrous nonwoven fabric sheets laminated together.

According to further another embodiment of the present invention, the urine disposal device includes a urine detecting structure at least having a liquid-permeable topsheet, a liquid-impermeable backsheet and the urine sensor and the urine collecting container both interposed between these sheets and a cover sheet to cover the urine detecting structure, wherein the first and second surface portions of the urination area are formed by doubling up the urine detecting structure.

Advantageous Effects of Invention

The urine disposal device for the urine detecting device according to the present invention is adapted to be directly put on the wearer's penis and provided with the urine sensor so that only urination may be quickly detected. The urine disposal device is provided with the urine collecting container connected to the external device and the voided urine may be automatically discharged outwardly. Consequently, even when a relatively large amount of urine is voided over a short period of time, the voided urine should not leak out from the urine disposal device. In addition, the second surface portion on which the urine collecting container is provided lies on the side of the wearer's body and the penis should not be pressed against the scrotum so as to compress the urethra, whereby the wearer may excrete urine with comfort.

BRIEF DESCRIPTION OF DRAWINGS

FIG. 7 (a) and FIG. 7 (b) are diagrams illustrating steps of assembling the urine disposal device.

DESCRIPTION OF EMBODIMENTS

First Embodiment

Figure 1:
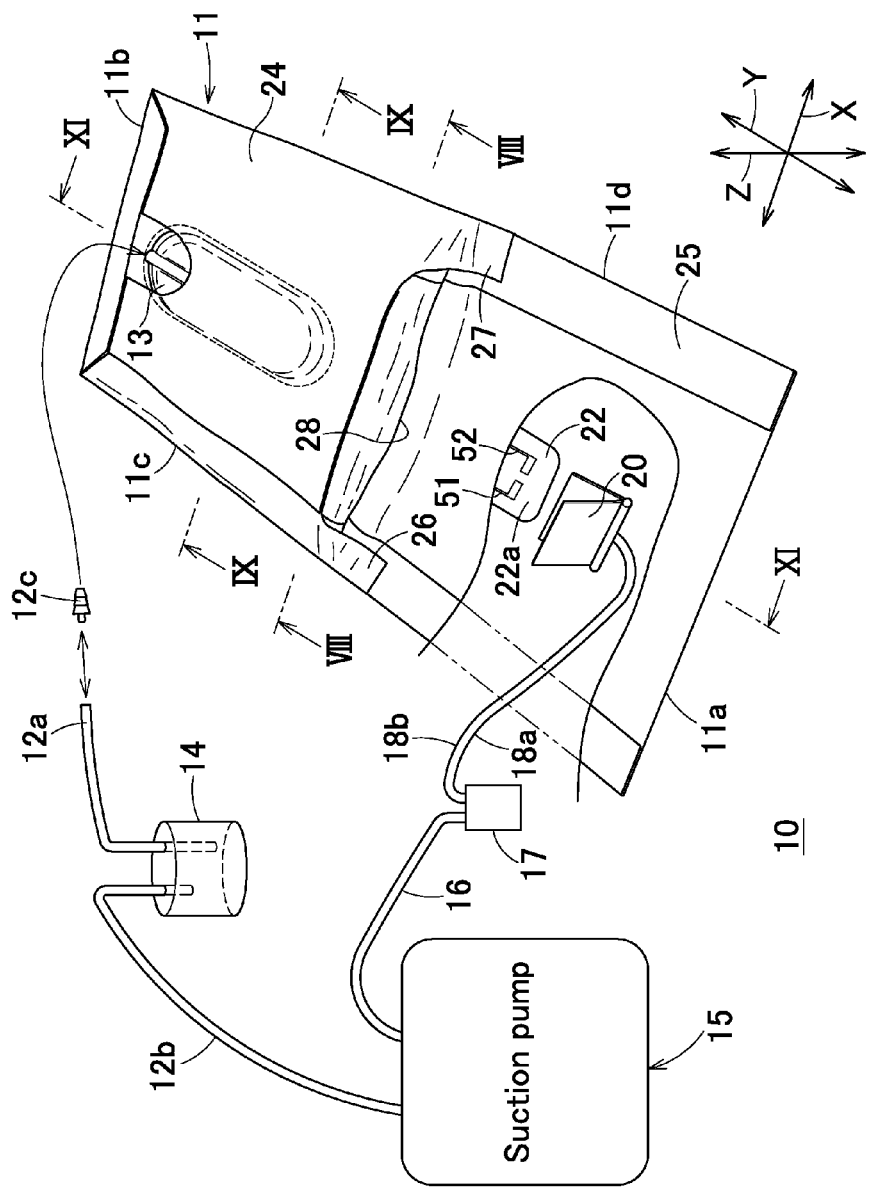
FIG. 1 is an overall schematic diagram of a urine detecting device according to a first embodiment of the present invention.

Referring to FIG. 1, a urine detecting device 10 in a first embodiment of the present invention includes a urine disposal device 11 and a urine reservoir 14 connected to a urine collecting container 13 of the urine disposal device 11 via a first suction tube 12a and a joint 12c. During use of the urine detecting device 10, a suction pump 15 is connected to the urine reservoir 14 via a second suction tube 12b.

A control unit 17 is connected to the suction pump 15 via an electric wiring 16 and an electric connector 20 is attached to leading ends of electric wirings 18a, 18b. The electric connector 20 is electrically connected to first and second electrodes 51, 52 provided on one end 22a of a urine sensor 22 extending outwardly from the urine disposal device 11. In the urine detecting device 10 having such overall structure, the suction pump 15 is actuated to vacuum up air within the urine reservoir 14 in response to the urine sensor 22 detecting that urine has been voided into the urine disposal device 11. When the air within the urine reservoir 14 is sucked, the voided urine is collected under the suction effect into the urine collecting container 13 and then collected into the urine reservoir 14 via the first suction tube 12a. The electric connector 20 is of a well known clip-type releasably clipping the end 22a of the sheet-like urine sensor 22 and provided on its inner surface with terminals adapted to be put in electrical contact with the first and second electrodes 51, 52 of the urine sensor 22, respectively.

In this regard, the urine reservoir 14, the suction pump 15 and the control unit 17 in the urine detecting device 10, except the urine disposal device 11, will be sometimes generically designated hereunder as external devices. While the urine disposal device 11 is electrically connected to the external devices in this embodiment, it is not essential to connect the urine disposal device 10 to the external devices electrically. For example, it is possible to provide the electric connector 20 with a small transmitter so that a disposal device provided in the control unit 17 may receive signals transmitted from the small transmitter and actuate the suction pump 15.

The urine disposal device 11 has a longitudinal direction Y, a transverse direction X being orthogonal to the longitudinal direction Y and a front-back direction (thickness direction) Z being orthogonal to both the longitudinal direction Y and the transverse direction X and includes first and second end edges 11a, 11b spaced apart from and opposite to each other in the longitudinal direction Y and lateral edges 11c, 11d spaced apart from and opposite to each other in the transverse direction X. In addition, the urine disposal device 11 has a pad-like urination area 24 within which the urine collecting container 13 and an extension flap portion 25 contiguous to the urination area 24 and extending from the urination area 24 in the longitudinal direction Y wherein the urination area 24 and the extension flap portion 25 have substantially the same length dimension in the longitudinal direction Y. The urination area 24 has sealing portions 26, 27 affixed to the lateral edges of the extension flap portion 25 and an opening 28 extending in the transverse direction X between the sealing portions 26, 27.

Figure 2:
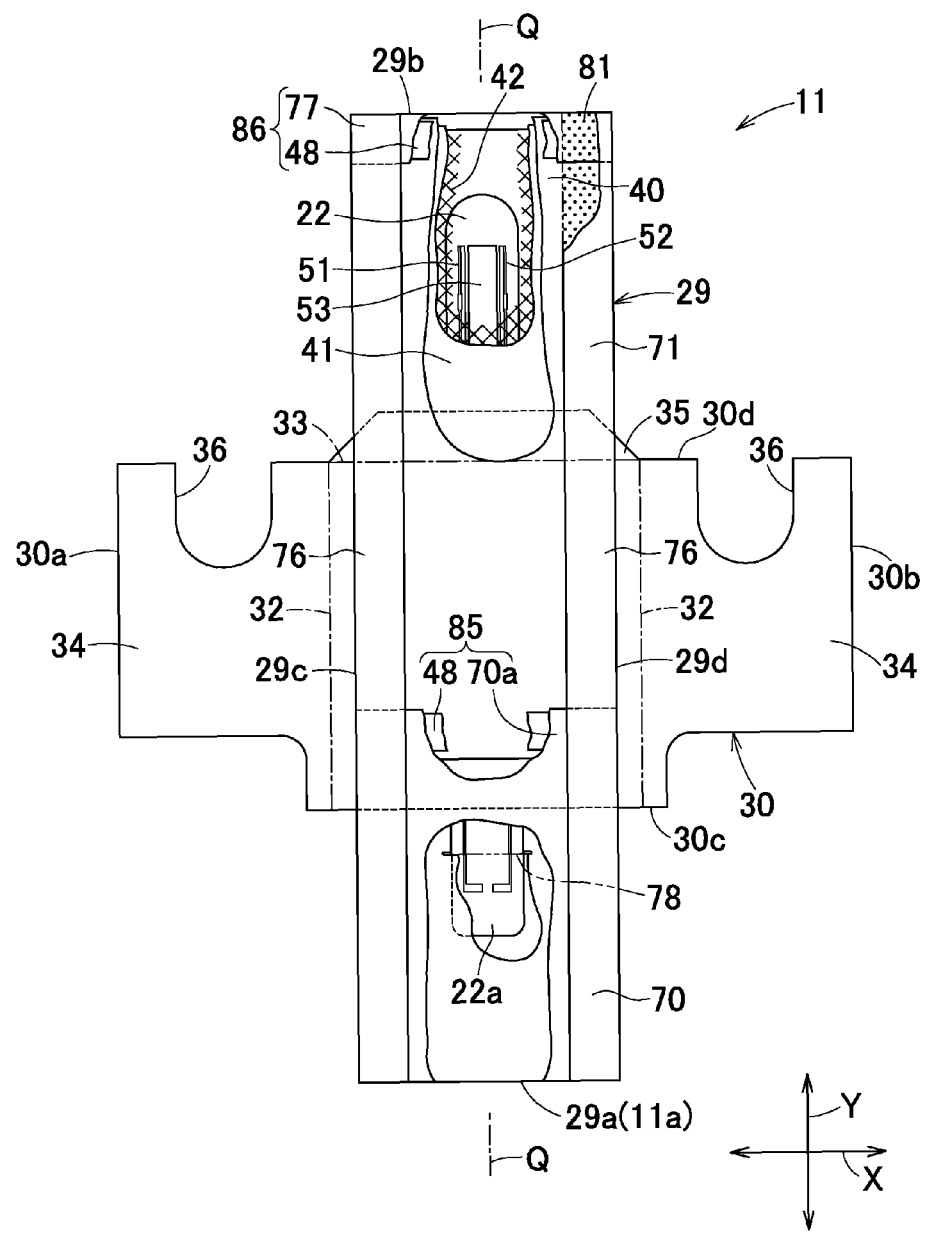
FIG. 2 is a partially cutaway developed plan view of a urine disposal device.

Referring to FIG. 2, the urine disposal device 11 includes a longitudinally long urine detecting structure 29 and a cover sheet 30 lying on the outer surface thereof. The urine detecting structure 29 has a first end edge 29a (corresponding to the first end edge 11a of the urine disposal device 11) and a second end edge 29b extending in the transverse direction and lateral edges 29c, 29d extending between these end edges in the longitudinal direction Y. The cover sheet 30 has first and second lateral edges 30a, 30b rectilinearly extending in the longitudinal direction Y and end edges 30c, 30d extending between these lateral edges in the transverse direction X and being convex outwardly along respective midportions. The cover sheet 30 further includes a pair of longitudinal fold lines 32 extending in the longitudinal direction Y in parallel to the lateral edges 29c, 29d of the urine detecting structure 29 provided on the inner surface of the cover sheet 30 and a transverse fold line 33 extending in the transverse direction X along the end edge 30d between the pair of longitudinal fold lines 32. Opposite lateral portions 34 are defined outboard of the pair of longitudinal fold lines 32 as viewed in the transverse direction X and an end flap 35 is defined outboard of the transverse fold line 33 as viewed in the longitudinal direction Y. The respective lateral portions 34 are formed along the end edge 30d with cutouts 36 which are concave inwardly.

Figure 3:
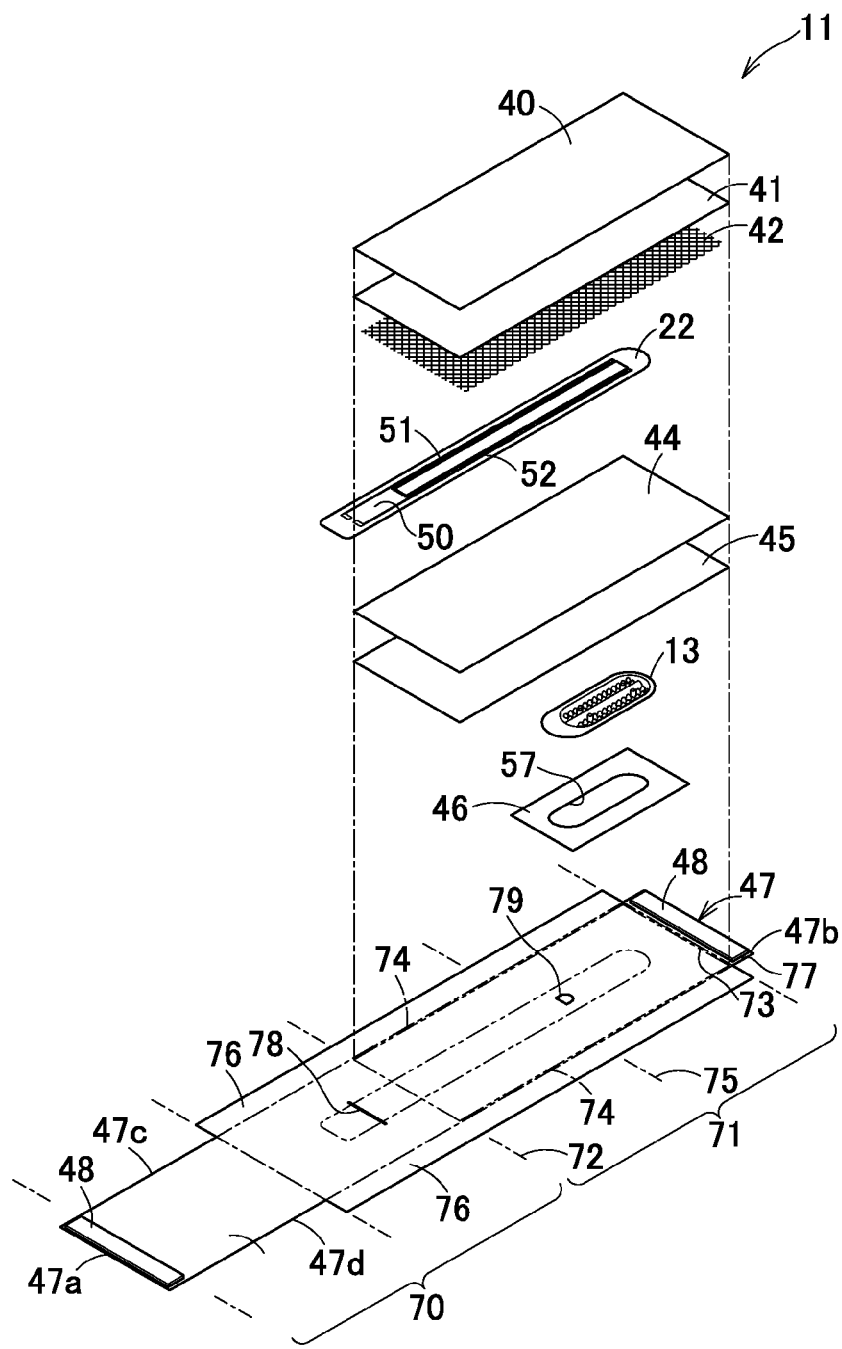
FIG. 3 is an exploded perspective view of the urine disposal device.

Referring to FIG. 3, the urine detecting structure 29 includes, in the order from the top to the bottom in its exploded perspective view, a liquid-permeable topsheet 40, a second sheet 41, an elastic rebound member 42 having elastic rebound properties, the urine sensor 22, a cushion sheet 44, a diffusion sheet 45, the tray-like urine collecting container 13, a low-air-permeable sheet 46 and a liquid-impermeable backsheet 47. An upper surface of the backsheet 47 is provided along opposite end edges with substantially leakage-barrier strips 48 respectively composed of a plurality of fibrous nonwoven fabric sheets laminated together.

The cover sheet 30 may be formed of a liquid-impermeable SMS fibrous nonwoven fabric or a spun bonded fibrous nonwoven fabric or a plastic sheet made of polyethylene or a laminate sheet thereof each having a mass per unit area in a range of about 10 to about 30 g/m$^2$.

The topsheet 40 may be formed of material selected from various kinds of liquid-permeable fibrous nonwoven fabric sheets, for example, an air-through nonwoven fabric having a mass per unit area in a range of about 20 to about 40 g/m$^2$. Similarly to the topsheet 40, the second sheet 41 also may be formed of material selected from various kinds of liquid-permeable fibrous nonwoven fabric sheets, for example, an air-through nonwoven fabric having a mass per unit area in a range of about 15 to about 25 g/m$^2$. The backsheet 47 may be formed of a liquid-impermeable SMS fibrous nonwoven fabric or a spun bonded fibrous nonwoven fabric or a plastic sheet made of polyethylene or a laminate sheet thereof having a mass per unit area in a range of about 10 to about 30 g/m$^2$.

The elastic rebound member 42 is a liquid-permeable mesh sheet formed of a soft synthetic resin such as ethylene-vinyl acetate copolymer and having an elastic rebound behavior and a thickness in a range of about 0.5 to about 1.0 mm. The elastic rebound member 42 may appropriately constrict the penis of a wearer having been inserted through the opening 28 into urination area 22 prevent the penis from being displaced and a portion of the voided urine from leaking out from the opening 28. Even after suction of voided urine, if the second sheet 41 remains in a wetted condition due to a portion of voided urine absorbed by the second sheet 41 and the second sheet 41 in such a wetted condition comes in direct or indirect contact with the urine sensor 22, for example, under the wearer's own weight, the portion of voided urine might be erroneously detected. However, the elastic rebound member 42 interposed between the second sheet 41 and the urine sensor 42 may prevent such malfunction. In this regard, the elastic rebound member 42 is affixed to the cushion sheet 44 preferably with an adhesive coated at some intervals to ensure that the liquid-permeability of the cushion sheet 44 is not inhibited by the adhesive.

Figure 4:
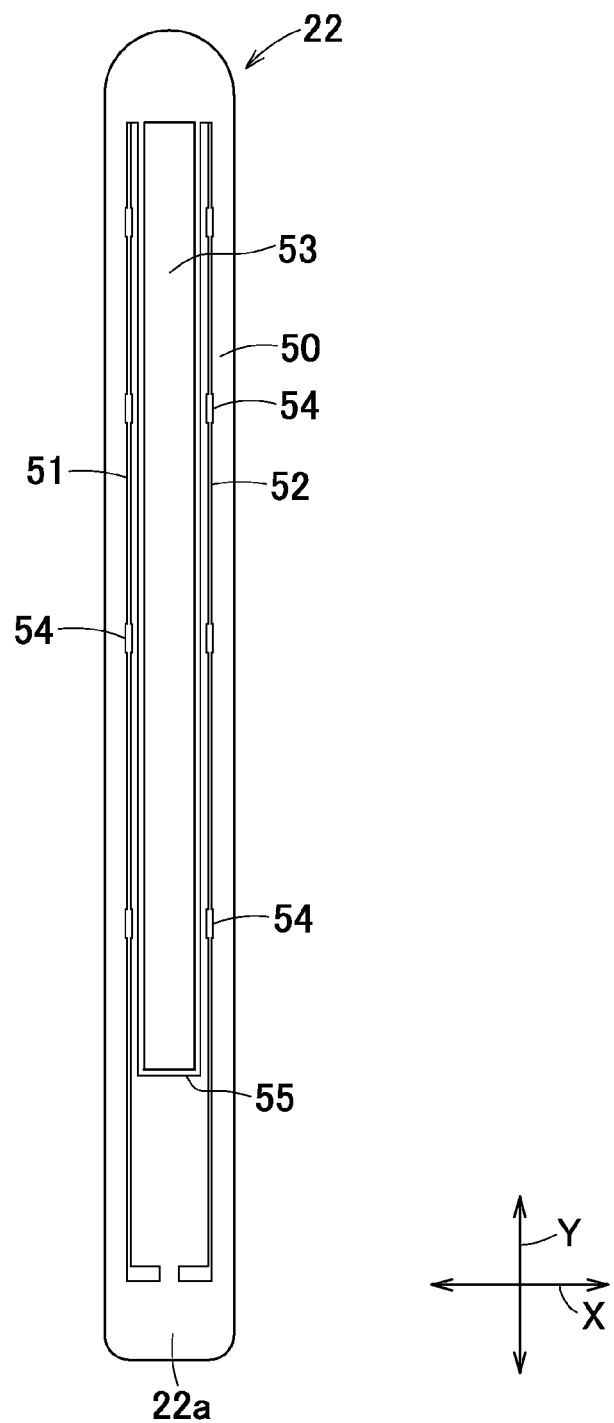
FIG. 4 is a scale-enlarged plan view of a urine sensor.

Referring to FIG. 4, the urine sensor 22 is composed of an insulating base sheet 50 formed of an elongate plastic film and first and second electrodes 51, 52 printed on the upper surface of the insulating base 50 with a conductive material such as a conductive ink and a conductive paint. For example, a polyester film having a thickness in a range of about 50 to about 100 μm printed with synthetic graphite such as carbon black in a range of about 3 to about 7% by mass or carbon graphite in a range of about 10 to about 30% by mass may be used. The insulating base sheet 50 is formed in a midsection thereof with a longitudinally long rectangular opening 53. The first and second electrodes 51, 52 are spaced apart from and opposed to each other by the intermediary of the opening 53 so as to extend in the longitudinal direction Y and the respective electrodes 51, 52 have a plurality of urine detecting portions 54, but these portions 54 are not always needed. The first and second electrodes 51, 52 are connected to each other by means of a relatively high electrical resistance region 55 extending along a periphery of the opening 53. In the urine sensor 22 arranged in this manner, voided urine diffuses over the diffusion sheet 45 upon urination and an electric current higher than the current usually carried in the high resistance region 55 is carried largely between the urine detecting portions 54 opposed to each other, thereby detecting an occurrence of urination.

The cushion sheet 44 is formed of a liquid-permeable nonwoven fabric sheet such as a thermal bond nonwoven fabric or an SMS nonwoven fabric and serves to prevent the urine being present in the diffusion sheet 45 and the low-air-permeable sheet 46 lying under the cushion sheet 44 from flowing back to the side of the electrodes.

The diffusion sheet 45 is formed of a liquid-permeable sheet such as a nonwoven fabric containing hydrophilic fibers, for example, rayon fibers, and used to, immediately upon occurrence of urination, diffuse the voided urine as rapidly as possible above the low-air-permeable sheet 46 so that the low-air-permeable sheet 46 may be wetted over a wide range thereof. When the low-air-permeable sheet 46 is turned to such a wet state, the internal space of the urine collecting container 13 is governed by a negative pressure which facilitates the voided urine to be sucked into the container 13.

The low-air-permeable sheet 46 is liquid-permeable and substantially or perfectly air-impermeable and as material of such low-air-permeable sheet 46, for example, it is possible to use an SMS nonwoven fabric or an SMS nonwoven fabric processed by surfactant so as to become hydrophilic. An air-permeability of the low-air-permeable sheet 46 is, for example, preferably in a range of 0 to 100 cc/cm$^2$/second in a wet condition and in a range of 20 to 200 cc/cm$^2$/second in a dry condition. The low-air-permeable sheet 46 is formed in its central region with an opening 57 in accordance with an external condition of a top opening 62 of the urine collecting container 13.

Figure 5:
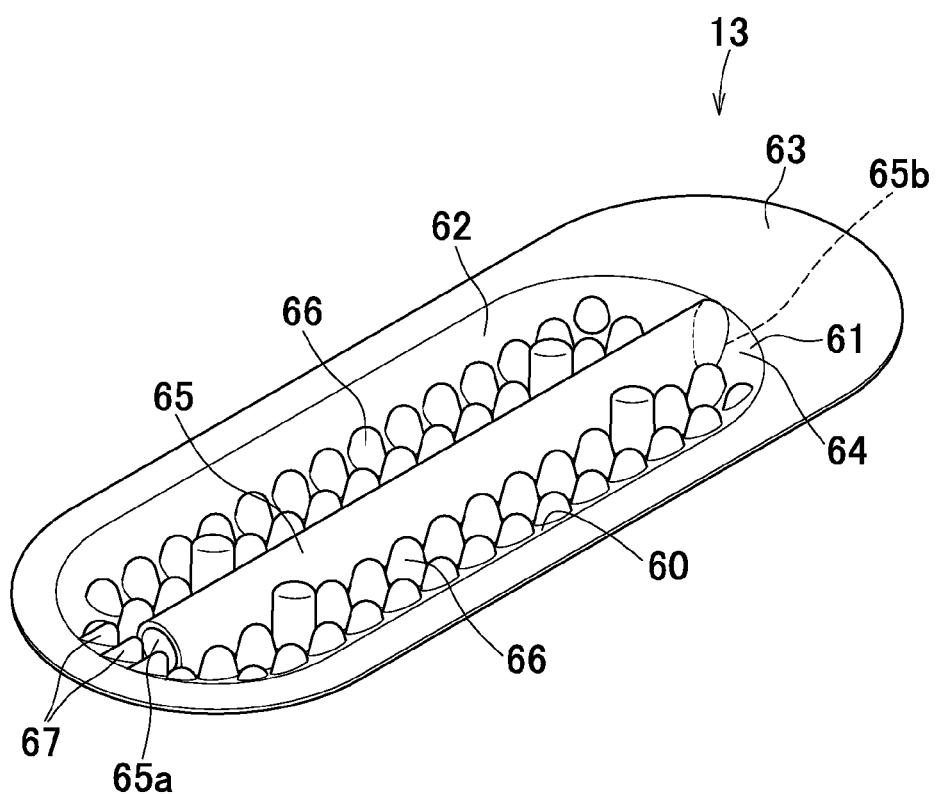
FIG. 5 is a scale-enlarged perspective view of a urine collecting container.

Referring to FIG. 5, the urine collecting container 13 is flexible, and may be formed with use of a soft, elastic and liquid-impermeable material such as soft polyethylene or silicon rubber. The urine collecting container 13 is flexible in the longitudinal direction Y and in the transverse direction X but has a sufficient degree of stiffness to resist against a deformation due to a negative pressure exerted thereto when the suction pump 15 sucks the voided urine. The urine collecting container 13 includes a bottom 60, a peripheral wall 61 spaced upwardly from the bottom 60, the top opening 62 and a peripheral flange portion 63 extending outwardly from an upper edge of the peripheral wall 61. The low-air-permeable sheet 46 is joined in a water-tight manner to the peripheral flange portion 63 with an adhesive and an internal space 64 is defined within the urine collecting container 13.

The urine collecting container 13 is formed with a tubular suction member 65 located generally in a middle in the transverse direction X of the container 13 so as to extend in the longitudinal direction Y and functioning to collect the voided urine flowing into the internal space 64 and to discharge this outwardly. The suction member 65 has a first opening 65a opened inwardly of the urine collecting container 13 and a second opening 65b opened outwardly of the urine collecting container 13 wherein the first suction tube 12a is connected to the second opening 65b by means of the joint 12c (See FIG. 1). On both sides of the suction member 65 in the transverse direction X, a plurality of protrusions 66 spaced upwardly from the bottom 60 are formed. The portion of the peripheral wall 61 opposed to the first opening 65a of the suction member 65 is formed with a plurality of protrusions 67 extending toward the first opening 65a.

Referring again to FIG. 3, the backsheet 47 is longitudinally longer than the other sheet members and has first and second end edges 47a, 47b, lateral edges 47c, 47d extending in the longitudinal direction Y between the end edges 47a, 47b, a first region 70 defining the extension flap portion 25 of the urine sensor 11 and a second region 71 continuously extending from the first region 70. The second region 71 is formed with first and second transverse fold lines 72, 73, a central fold line 75 extending in the transverse direction X and a pair of longitudinal fold lines 74 extending from the second region 71 to the first region 70 in the longitudinal direction Y along the opposite lateral edges 47c, 47d. Opposite side flaps 76 are formed outside the second transverse fold line 73 as viewed in the transverse direction X, an end flaps 77 is formed outside the second transverse fold line 73 as viewed in the longitudinal direction Y and the leakage-barrier sheet 48 is affixed to the inner surface of the end flap 77 with a hot melt adhesive (not shown). The first region 70 is formed at a position relatively closer to the second region 71 with a slit 78 extending in the transverse direction X and the second region 71 is formed in vicinities of the central fold line 75 with a substantially semi-circular exposure opening 79.

The urine disposal device 11 having such configuration may be assembled by the following steps described hereunder. First, the liquid-permeable sheet 40, the second sheet 41, the elastic rebound member 42, the urine sensor 22, the cushion sheet 44 and the diffusion sheet 45 are stacked in this order from the side of the skin-facing surface attached with a hot melt adhesive (not shown) coated at some intervals to contact surfaces of each pair of the adjacent sheets or layers. The urine sensor 22 has a length dimension in the longitudinal direction Y larger than that of the other sheet members and, in consequence, extends outwardly from the laminate of these sheets in the longitudinal direction Y. Particularly for the urine sensor 22, the hot melt adhesive is coated at some intervals preferably without any possibility that a function of a urine detecting circuit included in the urine sensor 22 might be disturbed. The diffusion sheet 45 is provided at a predetermined position of its inner surface with the low-air-permeable sheet 46 affixed thereto with a hot melt adhesive (not shown). In the low-air-permeable sheet 46 and the urine collecting container 13, the peripheral flange portion 63 of the urine collecting container 13 is affixed to the inner surface of the low-air-permeable sheet 46 with a hot melt adhesive (not shown) so that the opening 57 of the low-air-permeable sheet 46 may communicate with the top opening 62 of the urine collecting container 13.

Now the assembly as described above placed at a predetermined position on the inner surface of the backsheet 47, more specifically, at a position on the inner surface of the second region 71 predetermined so that the second opening 65b may be aligned with the exposure opening 79 the first suction tube 12a extending from the urine reservoir 14 may be connected with the second opening 65b of the tubular suction member 65 which is the constituent of the urine collecting container 13 by means of the joint 12c. The end 22a of the urine sensor 22 is inserted through the slit 78 of the first region 70 so as to be exposed outwardly.

Now, referring to FIGS. 6(a) and 6(b), a sub-region of the first region 70 defined on the side of the second end edge 47b is folded inwardly along the fold line 80 extending in the transverse direction X in the first region 70 so as to overlap the opposed inner surface of the first region 70 and the leakage-barrier sheet 48 is placed on the inner surface of the topsheet 40 and joined thereto with a hot melt adhesive (not shown). The end flap 77 of the backsheet 47 is folded inwardly along the fold line 73 and the leakage-barrier sheet 48 lying on the inner surface of the end flap 77 is joined to the inner surface of the topsheet 40 with a hot melt adhesive (not shown). Then, the side flaps 76 of the backsheet 47 are folded inwardly along the longitudinal fold lines 74 and joined to the leakage-barrier sheet 48, the topsheet 40 and the first region 70 of the backsheet 47 respectively facing the respective inner surfaces of the side flaps 76 with a hot melt adhesive 81 coated to the inner surfaces of the side flaps 76.

Figure 6:
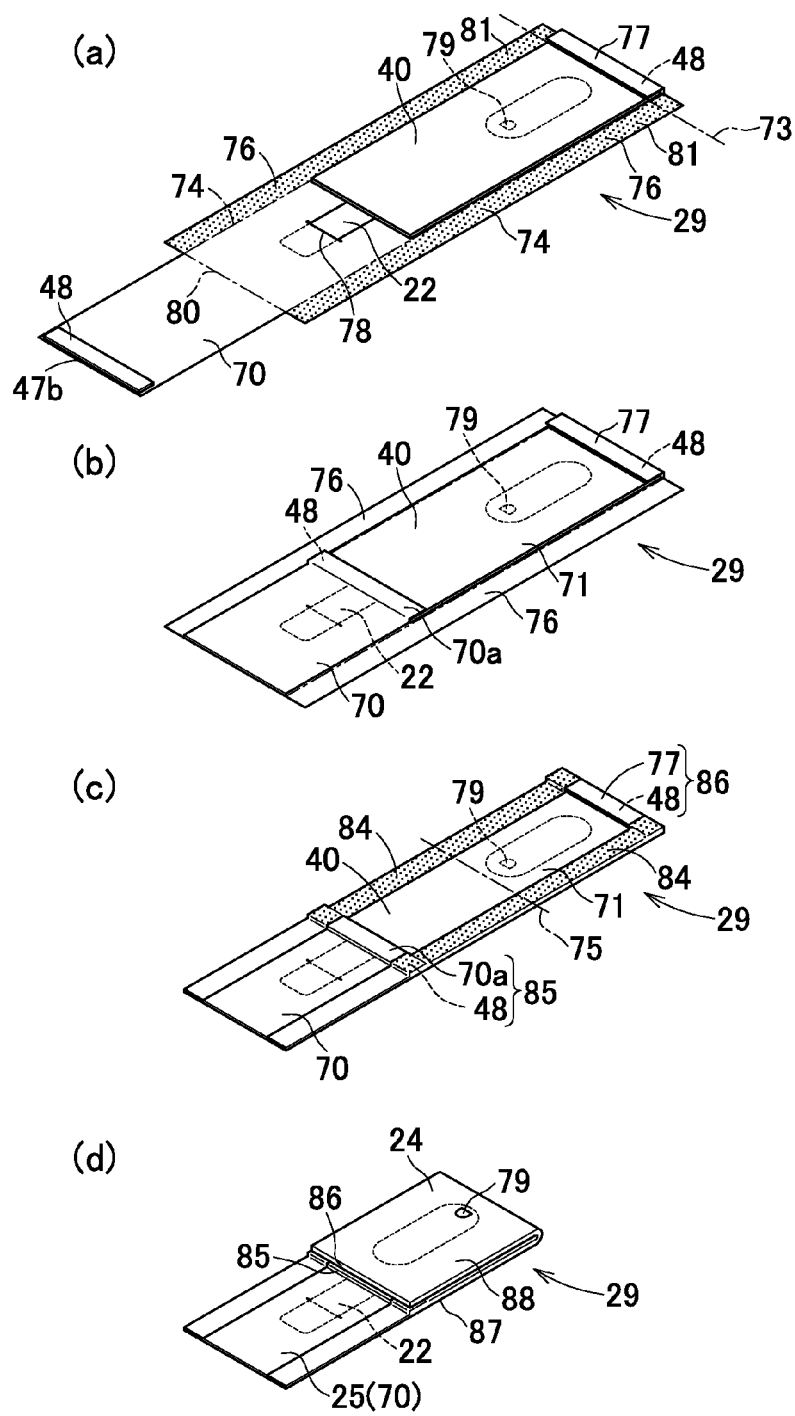
FIG. 6 (a)-FIG. 6 (d) are diagrams illustrating steps of assembling the urine disposal device.

In this way, as illustrated in FIG. 6 (c), a first leakage-barrier 85 composed of an end 70a of the first region 70 of the backsheet 47 and the leakage-barrier sheet 48 and a second leakage-barrier 86 opposed to and spaced apart from the first leakage-barrier 85 and composed of the end flap 77 of the backsheet 47 and the leakage-barrier sheet 48 are formed between the side flaps 76. In this regard, it is also possible to form the first and second leakage-barriers 85, 86 from only the leakage-barrier sheet 48 affixed to the inner surface of the topsheet 40.

Then, along the central fold line 75 extending in the transverse direction X across the midsection of the second region 71 of the backsheet 47a, one half sub-region of the second region 71 is folded onto opposed half sub-region of the second region 71 so as to overlap the respective halves of the side flaps 76 with each other and to attach the respective halves to themselves with a hot melt adhesive 84 applied to the respective skin-facing surfaces of the side flaps 76. In consequence, the urine detecting structure 29 is held in a doubled up state as illustrated in FIG. 6 (d). The urination area 24 of the urine detecting structure 29 has a first surface portion 87 and a second surface portion 88 folded onto each other and the first region 70 continuously extending from the second surface portion 87 defines the extension flap portion 25 of the urine disposal device 11.

Referring to FIGS. 7(a) and 7(b), the urine detecting structure 29 is placed on the inner surface of the cover sheet 30 and affixed to the inner surface with a hot melt adhesive 90. The end flap 35 is folded inwardly along the transverse fold line 33 and joined to the second surface portion 88 of the urine detecting structure 29, then one of the lateral portions 34 is folded inwardly along the associated longitudinal fold line 32 and joined to the second surface portion 88 with the hot melt adhesive 90 and the other of the lateral portions 34 is folded along the associated longitudinal fold line 32 and affixed to the one of the lateral portions 34 having been affixed to the second surface portion 88, with the hot melt adhesive 90. In this regard, the end flap 35 having been folded and affixed to the second surface portion 88 of the urine detecting structure 29 and the lateral portions 34 are not in an overlapping state and the lateral portions 34 of the cover sheet 30 respectively have a length dimension smaller than the respective length dimension in the transverse direction X of the first surface portion 87 and the second surface portion 88 and consequently the first end edge 30a of the cover sheet 30 lies medial to the lateral edges 11d of the urine disposal device 11.

Figure 8:
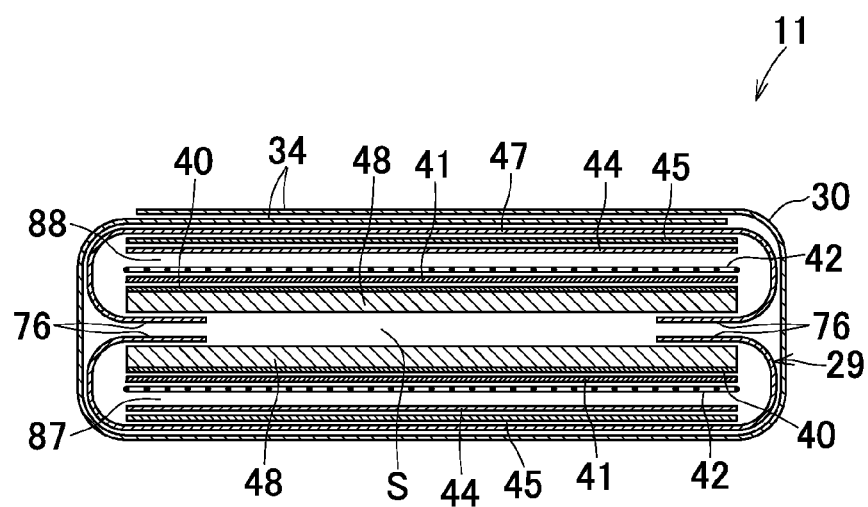
FIG. 8 is a scale-enlarged sectional view taken along line VIII-VIII in FIG. 1.
Figure 9:
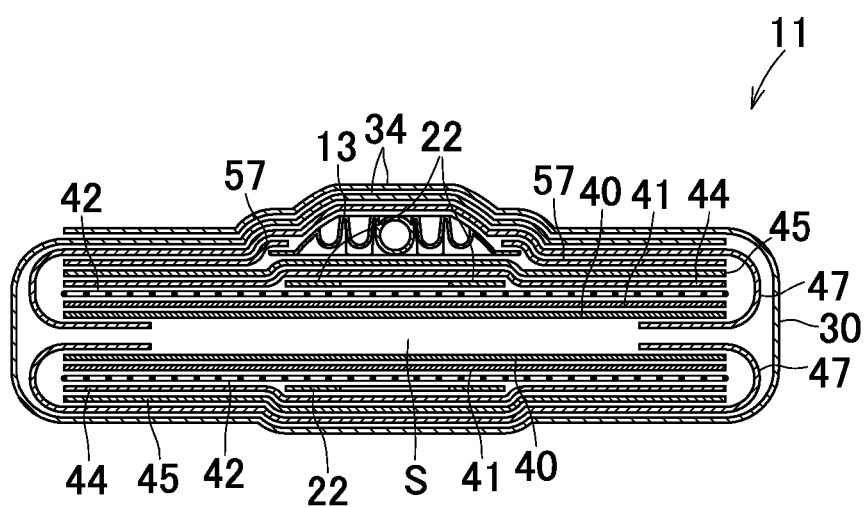
FIG. 9 is a scale-enlarged sectional view taken along line IX-IX in FIG. 1.

Referring now to FIGS. 8 and 9, operation of the urine disposal device 11 and the urine detecting device 10 utilizing this urine disposal device 11 in response to urination will be described hereunder. Urine voided in the urination area 24 of the urine disposal device 11 is temporarily retained within the penis receiving space S. The urine temporarily retained within the penis receiving space S permeates the topsheet 40 through the first surface portion 87 and the second surface portion 88, then passes through the second sheet 41 and the elastic rebound member 42 and quickly comes in contact with the urine sensor 22. When urine continuously remains in contact with a gap between the first and second electrodes 51, 52 constituting the urine sensor 22, electric current having a current value higher than that of electric current which is usually carried in the detecting circuit is carried between the urine detecting portions 54. When such higher current value exceeds a predetermined threshold value preset in the control unit 17, urination is detected.

Upon detection of urination, the control unit 17 transmits a detection signal to an electric motor for the suction pump 15 and, in response to the detection signal, the electric motor is driven to actuate the suction pump 15. Actuation of the suction pump 15 vacuumizes the urine reservoir 14 and, as a result, voided urine having been collected in the internal space 64 is sucked via the first suction tube 12a into the urine reservoir 14. In this way, the voided urine is discharged out from the urine disposal device 29. After the voided urine has been discharged out from the urine disposal device 29, if there is no urine remaining in contact with the urine detecting portions 54 of the first and second electrodes 51, 52, the current value drops and, transmission of the signal from the control unit 17 to the electric motor for the suction pump 15 stops. In consequence, the suction pump 15 is not actuated any more. In this manner, the urine detecting device 10 according to the present invention not only makes it possible to detect urination and to inform the care person being away from the patient of occurrence of urination but also to collect the voided urine into the collecting container 13 and to discharge the voided urine out instantaneously from the collecting container 13 into the urine reservoir 14 via the suction pump 15 thereby discharging the voided urine outwardly from the urine disposal device 11.

The penis receiving space S defined within the urination area 24 is the space double-sealed by the side flaps 76 of the backsheet 47 and the lateral portions 34 of the cover sheet 30. Therefore, even if a small amount of urine voided into the penis receiving space S leaches out through the side flaps 76, such amount of urine should not leak out from the urine disposal device 11.

In this regard, it is also possible to form the urine disposal device 11 by following assembling steps different from those as have been described above. For example, the first surface portion 87 and the second surface portion 88 may be integrally formed.

Figure 10:
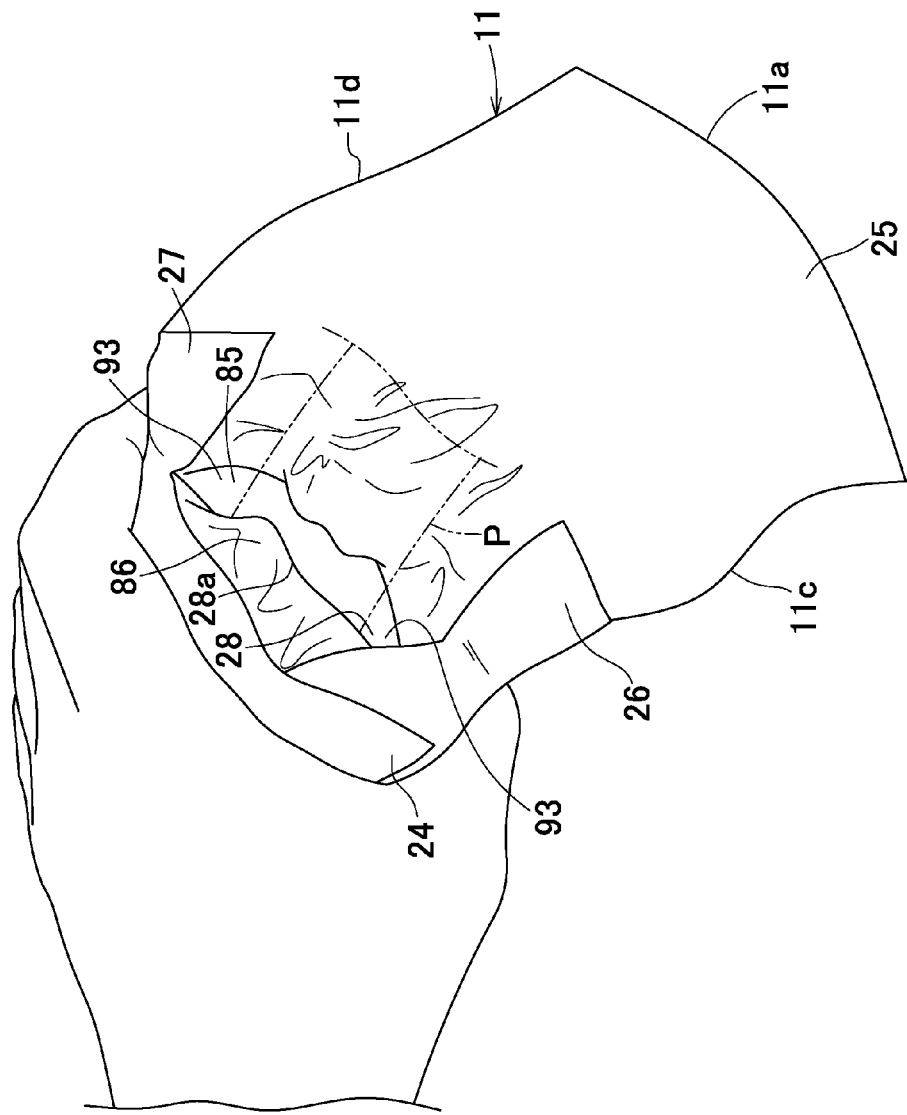
FIG. 10 is a diagram illustrating the urine disposal device put on the wearer's body.
Figure 11:
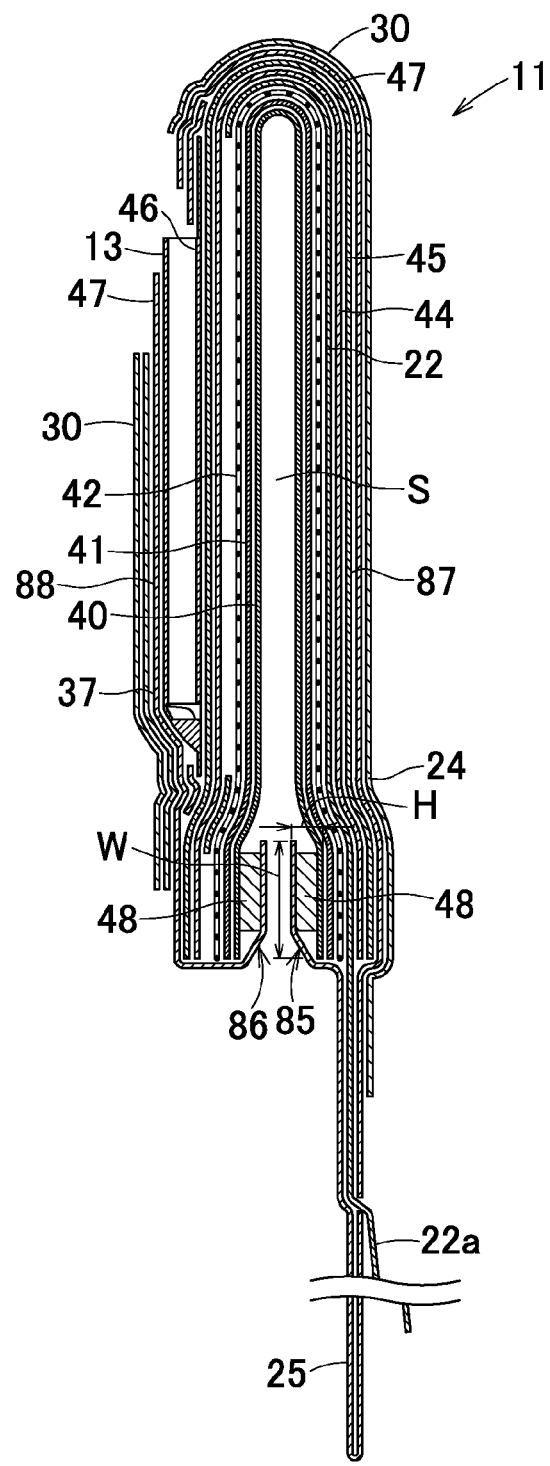
FIG. 11 is a scale-enlarged sectional view taken along line XI-XI in FIG. 1.
Figure 12:
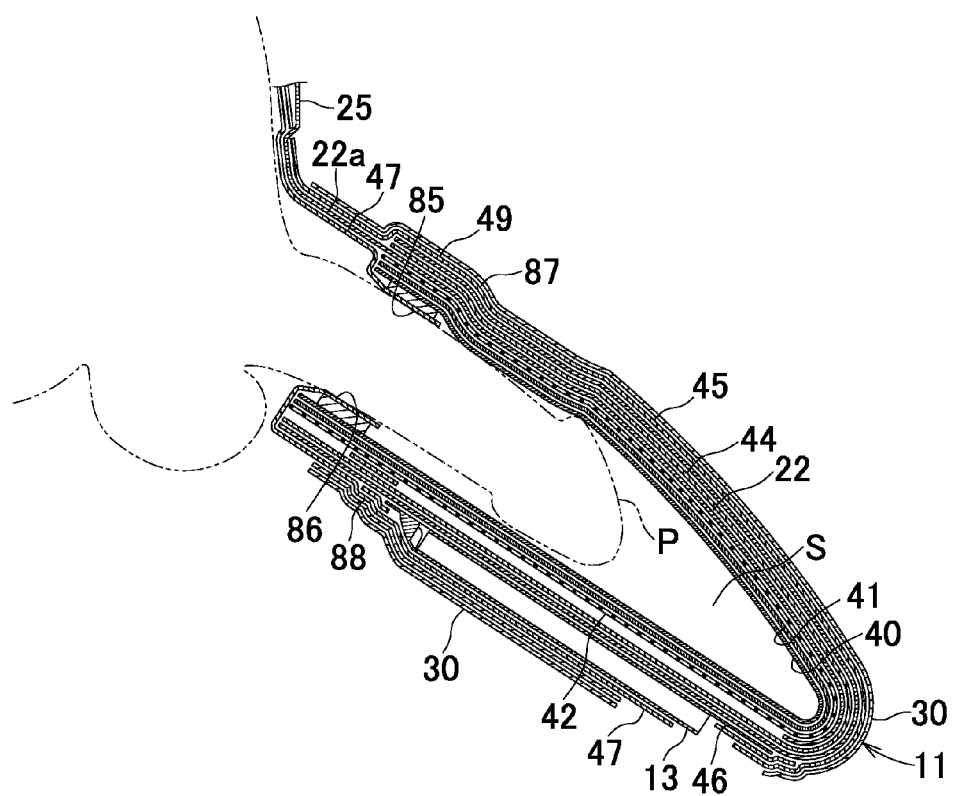
FIG. 12 is a sectional view similar to FIG. 11, illustrating a situation in which the urine disposal device has been put on penis.
Figure 13:
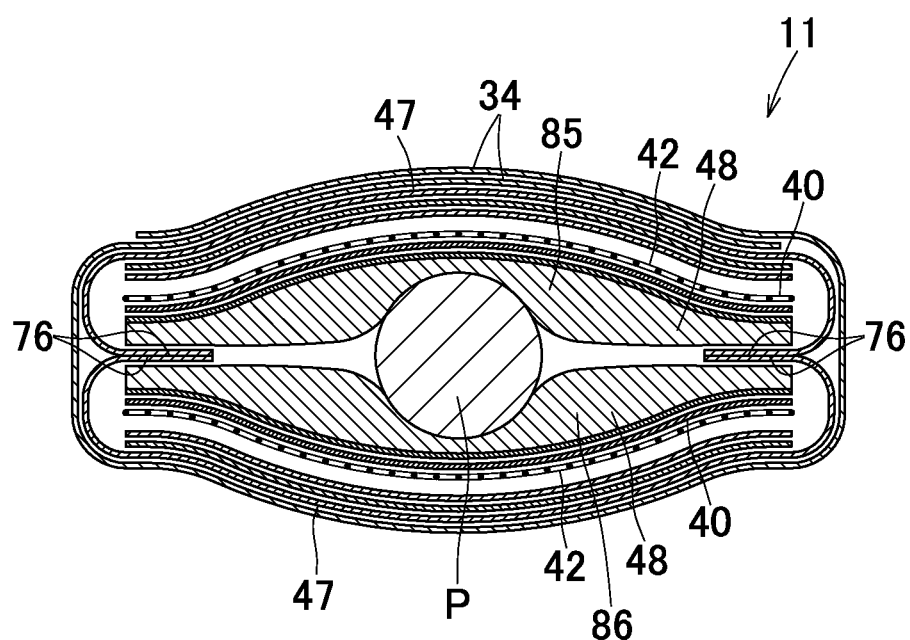
FIG. 13 is a sectional view similar to FIG. 8, illustrating a situation in which the urine disposal device has been put on penis.

FIG. 10 is a diagram illustrating the urine disposal device 11 put on the wearer's body, FIG. 11 is a scale-enlarged sectional view taken along line XI-XI in FIG. 1, FIG. 12 is a sectional view similar to FIG. 11, illustrating the urine disposal device 11 in a state being put on the wearer's penis P and FIG. 13 is a sectional view similar to FIG. 8, illustrating the urine disposal device 11 in a state being put on the wearer's penis P.

Referring to FIG. 10, when it is desired to put the urine disposal device on the wearer's body, the both sides of the urine disposal device 11 gripped with both the hands are pushed inwardly so as to deform the opening's periphery 28a until the opening 28 is spread out sufficiently to define gaps 93 on both sides of the wearer's penis P and then the wearer's penis P is inserted into the penis receiving space S. Then, with the wearer's penis P being held within the penis receiving space S, the urine disposal device 11 is turned upside down so that the extension flap portion 25 may be put in contact with a lower abdominal region of the wearer (See FIG. 12) and the hands are released from the urine disposal device 11. The elastic rebound member 42 is formed of material having an elastic rebound force such as EVA (ethylene-vinyl acetate copolymer resin) which is superior in the elastic rebound property as well as in the elastic restoring property to the natural or synthetic rubber conventionally used as material of the elastic member in this type of bodily fluid-handling articles.

Such relatively high elastic rebound force of the elastic rebound member 42 facilitates a buckling distortion of the opening's periphery 28a under a force exerted thereon to spread up the opening 28 sufficiently to form the gaps on both sides of the wearer's penis P. In consequence, the urine disposal device 11 may be rather easily put on the wearer's penis P. When the hands are released from the urine disposal device 11 after the urine disposal device 11 has been put on the wearer's penis P, the opening's periphery 28a is closed under the elastic storing force of the elastic rebound member 42. Namely, the urine disposal device 11 may be put on the wearer's penis P without touching the penis P with hands. This is preferable from a sanitary view point.

While the elastic rebound member 42 may be attached only the opening's periphery 28a in one of the front and second surface portions 87, 88 so long as the above-mentioned advantageous effect is ensured, entire area of both the first surface portion 87 and the second surface portion 88 may be provided with the elastic rebound members 42 to assure that the wearer's penis P inserted into the penis receiving space S may be stably held within this space S and the urine disposal device 11 should not easily come off from the wearer's body even under any external force exerted thereon.

Referring to FIG. 11, the opening's periphery 28a of the first surface portion 87 in the urination area 24 is formed with the first leakage-barrier 85 extending in the transverse direction X between the sealing portions 26, 27 and the opening's periphery 28 of the second surface portion 88 is formed with the second leakage-barrier 86 spaced apart from and opposed to the first leakage-barrier 85 in the front-back direction Z. As has previously been described, the first and second leakage-barriers 85, 86 are partially composed of the leakage-barrier sheets formed of a plurality of fibrous nonwoven fabric layers and consequently have a sufficient thickness to prevent the urine voided into the penis receiving space S from leaking out through the opening 28.

Referring to FIG. 12, in a state that the urine disposal device 11 is put on the penis P, the first surface portion 87 of the urination area 24 extends outwardly in the longitudinal direction Y beyond the second surface portion 88. In this state, the first and second leakage-barriers 85, 86 are kept in contact with the proximal portion of the penis P under the elastic rebound force of the elastic rebound member 42 and the extension flap portion 25 of the first surface portion 87 extending outwardly in the longitudinal direction Y from the second surface portion 88 is kept in contact with the lower abdominal region of the wearer. For the reason that the extension flap portion 25 is kept in contact with the wearer's lower abdominal region on the side of the first surface portion 87 and the opening' periphery 28a of the urine disposal device 11 is kept in close contact with the penis P, the urine disposal device 11 should not drop off from the penis P and/or urine should not leak out through the opening 28 even if the opening 28 faces downward. Additionally, in the extension flap 25 kept in contact with the wearer's lower abdominal region, the backsheet 47 lies on the inner side of the end 22a of the urine sensor 22 and therefore the end 22a should not be put in direct contact with the wearer's body. As a result, the urine sensor 22 formed of a plastic film should not come in contact with the wearer's skin and an uncomfortable irritation against the wearer's skin may be avoided.

Referring to FIG. 13, the penis P having been inserted into the penis receiving space S is appropriately constricted by the first and second leakage-barriers 85, 86 having a cushioning property along the opening's periphery under the elastic effect of the elastic rebound member 42 and thus comes into a condition as if the periphery of the penis P is wrapped with the first and second leakage-barriers 85, 86. In consequence, the gaps 93 formed on both sides of the penis P in the course of putting the urine disposal device 11 on the penis P is reduced and urine once voided into the penis receiving space S should not easily leak out along the penis through the gaps.

Particularly when the wearer assumes a recumbent position, the urine disposal device 11 takes a posture parallel to a floor surface. However, even in such a posture, the urine disposal device 11 is kept in tight contact with the penis P by the first and second leakage-barriers 85, 86 and, in addition, the voided urine is rapidly discharged outwardly without leaking out through the opening 19. Additionally, the voided urine is quickly collected into the urine collecting container 13 and, therefore, even if relatively large amount of urine is voided over a short period of time, urine should not leak out. While, in the conventional urine absorbent pad designed so as to be put on the wearer's body with the wearer's penis inserted through the opening, an own weight of urine absorbed and retained by the pad body might be loaded on the wearer's penis P to compress the urethra and create a sense of discomfort against the wearer, the urine disposal device 11 according to this embodiment quickly discharges the voided urine outwardly to assure that the wearer may excrete urine with comfort without compressing the urethra.

Referring again to FIG. 11, to ensure that the first and second leakage-barriers 85, 86 produce such advantageous effect, the respective leakage-barriers 85, 86 preferably have a thickness H (dimension in the front-back direction Z) in a range of about 3.0 to about 15.0 mm and a width dimension W (length dimension in the longitudinal direction Y) in a range of about 10.0 to about 40.0 mm, depending on a size of the urine disposal device 11 as a whole.

Figure 14:
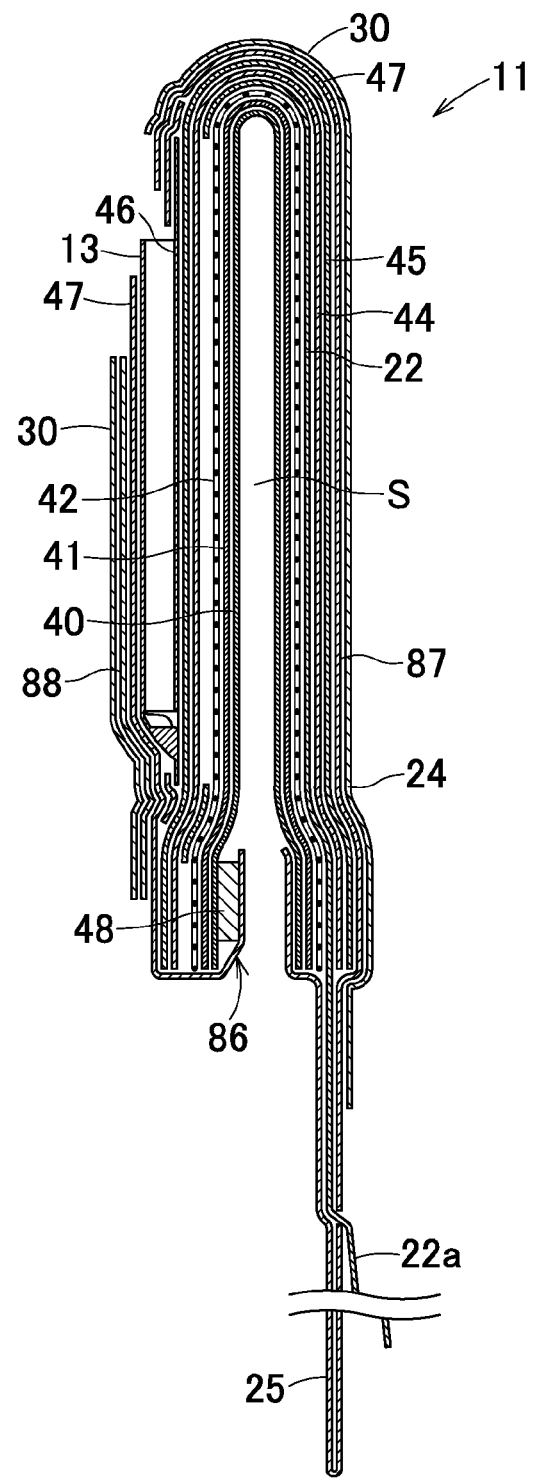
FIG. 14 is a sectional view similar to FIG. 11, illustrating a second embodiment.

FIG. 14 is a sectional view similar to FIG. 11, illustrating the urine detecting device 10 according to a second embodiment of the present invention. The urine detecting device 10 according to this embodiment is substantially the same as that according to the first embodiment and only features distinguished from those in the first embodiment will be described hereunder.

According to this embodiment, in the opening's periphery 28a of the urine disposal device 11, only the second leakage-barrier 86 of the first and second leakage-barriers 85, 86 is formed. In such embodiment also, the second leakage-barrier 86 sufficiently blocks movements of urine to the opening 28 and the opening's periphery 28a is surely kept in close contact with the penis P under the elastic rebound force of the elastic rebound member 42 and urine should not leak out through the opening 28. So long as such advantageous effect may be ensured, at least one of the first and second leakage-barriers 85, 86 may be formed and, as still another embodiment, it is also possible to form only the first leakage-barrier 85 instead of the second leakage-barrier 86.

The respective constituent members of the urine detecting device 10 and the urine disposal device 11 are not limited to those described in this description but the other various types of material widely used in the relevant technical field may be used without limitation. The terms "first" and "second" used in the description and Claims of the present invention are used merely to distinguish the similar elements, similar positions or the other similar factors.

REFERENCE SIGNS LIST 10 urine detecting device
11 urine disposal device
13 urine collecting container
15 suction pump
22 urine sensor
24 urination area
28 opening
28a opening's periphery
29 urine detecting structure
30 cover sheet
40 topsheet
42 elastic rebound member
47 backsheet
85 first leakage-barrier
86 second leakage-barrier
87 first surface portion
88 second surface portion
P penis
Y longitudinal direction
Z front-back direction

The invention claimed is:

1. A urine disposal device for use with a urine detecting device including a urine sensor adapted to detect urination, wherein said urine disposal device comprises:
    a front-back direction and includes a urination area having a first surface portion and a second surface portion cooperating to cover a penis of a wearer in the front-back direction and an opening extending in a width direction of the urination area through which the penis is inserted;
    the urination area has a urine collecting container and the second surface portion lies on the side of the wearer's body; and
    the urine disposal device includes a urine detecting structure at least having a liquid-permeable topsheet, a liquid-impermeable backsheet and the urine sensor and the urine collecting container both interposed between these sheets and a cover sheet wherein the first and second surface portions of the urination area are formed by doubling up the urine detecting structure.

2. The urine disposal device according to claim 1, wherein an opening's periphery in at least one of the first and second surface portions is provided with an elastic rebound member extending in the urination area.

3. The urine disposal device according to claim 2, wherein the opening's periphery provided with the elastic rebound member is provided with a leakage-barrier having a predetermined thickness.

4. The urine disposal device according to claim 3, wherein the urine disposal device has a longitudinal direction and the first surface portion extends outwardly in the longitudinal direction beyond the second surface portion.

5. The urine disposal device according to claim 4, wherein the leakage-barrier is a fibrous nonwoven fabric layer composed of a plurality of fibrous nonwoven fabric sheets laminated together.

6. The urine disposal device according to claim 3, wherein the leakage-barrier is a fibrous nonwoven fabric layer composed of a plurality of fibrous nonwoven fabric sheets laminated together.

7. The urine disposal device according to claim 2, wherein the urine disposal device has a longitudinal direction and the first surface portion extends outwardly in the longitudinal direction beyond the second surface portion.

8. The urine disposal device according to claim 2, wherein a leakage-barrier is a fibrous nonwoven fabric layer composed of a plurality of fibrous nonwoven fabric sheets laminated together.

9. The urine disposal device according to claim 1, wherein an opening's periphery provided with an elastic rebound member is provided with a leakage-barrier having a predetermined thickness.

10. The urine disposal device according to claim 9, wherein the urine disposal device has a longitudinal direction and the first surface portion extends outwardly in the longitudinal direction beyond the second surface portion.

11. The urine disposal device according to claim 9, wherein the leakage-barrier is a fibrous nonwoven fabric layer composed of a plurality of fibrous nonwoven fabric sheets laminated together.

12. The urine disposal device according to claim 1, wherein the urine disposal device has a longitudinal direction and the first surface portion extends outwardly in the longitudinal direction beyond the second surface portion.

13. The urine disposal device according to claim 12, wherein a leakage-barrier is a fibrous nonwoven fabric layer composed of a plurality of fibrous nonwoven fabric sheets laminated together.

14. The urine disposal device according to claim 1, wherein a leakage-barrier is a fibrous nonwoven fabric layer composed of a plurality of fibrous nonwoven fabric sheets laminated together.

\* \* \* \* \*